(12) United States Patent
Son et al.

(10) Patent No.: US 10,492,731 B2
(45) Date of Patent: Dec. 3, 2019

(54) METHOD AND APPARATUS FOR FOCUSING MICROWAVE AND THERMALLY IMAGING FOR BIOLOGICAL TISSUE

(71) Applicant: Electronics and Telecommunications Research Institute, Daejeon (KR)

(72) Inventors: Seong Ho Son, Daejeon (KR); Jong Hwa Kwon, Daejeon (KR); Soon Ik Jeon, Daejeon (KR); Hyung Do Choi, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 932 days.

(21) Appl. No.: 15/071,477

(22) Filed: Mar. 16, 2016

(65) Prior Publication Data
US 2016/0287086 A1     Oct. 6, 2016

(30) Foreign Application Priority Data

Apr. 2, 2015   (KR) ........................ 10-2015-0046690
Jan. 19, 2016   (KR) ........................ 10-2016-0006633

(51) Int. Cl.
*A61B 5/00*     (2006.01)

(52) U.S. Cl.
CPC .... *A61B 5/7257* (2013.01); *A61B 2562/0228* (2013.01)

(58) Field of Classification Search
CPC .......... A61B 2562/0228; A61B 5/0507; A61B 5/7257; A61B 18/1815; A61B 2018/00636; A61B 5/0033; A61B 5/0093; A61B 5/01; A61B 5/015; A61B 5/7225; A61N 5/02; A61N 5/045
See application file for complete search history.

(56) References Cited

U.S. PATENT DOCUMENTS

| | | | | |
|---|---|---|---|---|
| 6,026,173 | A | * | 2/2000 | Svenson ................. A61B 5/05 382/131 |
| 2006/0241410 | A1 | * | 10/2006 | Fang ........................ A61B 5/05 600/430 |
| 2009/0198112 | A1 | | 8/2009 | Park et al. |
| 2012/0172954 | A1 | | 7/2012 | Zastrow et al. |
| 2013/0059550 | A1 | | 3/2013 | Kwak et al. |
| 2015/0042508 | A1 | | 2/2015 | Etri |

FOREIGN PATENT DOCUMENTS

| | | |
|---|---|---|
| KR | 19940000191 B1 | 1/1994 |
| KR | 1020070060968 A | 6/2007 |

OTHER PUBLICATIONS

Mark Haynes, "Real-time Microwave Imaging of Differential Temperature for Thermal Therapy Monitoring," Jun. 2104, IEEE Transactions on Biomedical Engineering, vol. 16, No. 6, pp. 1787-1797.*

* cited by examiner

*Primary Examiner* — Joel Lamprecht
(74) *Attorney, Agent, or Firm* — William Park & Associates Ltd.

(57) ABSTRACT

An exemplary embodiment of the present invention discloses a microwave signal processing method and apparatus which precisely focus a microwave onto a specific part of a biological tissue and rapidly images a temperature distribution in the biological tissue generated thereby.

15 Claims, 4 Drawing Sheets

METHOD AND APPARATUS FOR FOCUSING MICROWAVE AND THERMALLY IMAGING FOR BIOLOGICAL TISSUE

CROSS-REFERENCE TO RELATED APPLICATIONS

This application claims priority to and the benefit of Korean Patent Application Nos. 10-2015-0046690 and 10-2016-0006633 filed in the Korean Intellectual Property Office on Apr. 2, 2015 and Jan. 19, 2016, respectively, the entire contents of which are incorporated herein by reference.

TECHNICAL FIELD

The present invention relates to a microwave signal processing method and apparatus, and more particularly, to a microwave signal processing method and apparatus which focus a microwave onto a specific part of a biological tissue such as a human body and monitor and control heat generated thereby.

BACKGROUND ART

Recently, a microwave has been applied to various application fields in addition to a wireless communication technology. For example, the microwave is applied as a local radio wave exposing unit which focuses a microwave onto a specific part in a human body to treat cancer or cause a significant reaction of a biological tissue. Current technologies which may be applied to such an application field include methods for focusing and illuminating radiation (for example, X-ray) having straightness or conducting an electric signal outside of a biological tissue, or radiating an electromagnetic signal over a broad part.

In the meantime, in order to focus an electromagnetic signal having diffraction or scattering characteristics, that is, a microwave onto a specific part in a biological tissue, a plurality of antennas is disposed outside the biological tissue and the microwave is focused through the antenna in accordance with a predetermined focusing method.

In this case, a method for precisely focusing a microwave onto a desired specific part of the biological tissue is required. Further, when a predetermined microwave is transmitted, it is also required to monitor whether the microwave is precisely focused onto a desired position. When the method is applied to a cancer treatment in the human body, if the microwave is focused on a normal tissue rather than a cancer tissue, the normal tissue may be damaged. Therefore, focusing accuracy is significantly important. Further, when the method is applied as a local radio wave exposing unit which causes a significant reaction of a biological tissue, in order to focus the microwave only onto a tissue of interest, the microwave needs to avoid being exposed onto other tissues. Therefore, the focusing accuracy is also important.

SUMMARY OF THE INVENTION

The present invention has been made in an effort to provide a microwave signal processing method and apparatus which precisely focus microwave onto a specific part of a biological tissue and rapidly images biological tissue internal temperature distribution generated thereby.

Technical objects of the present invention are not limited to the aforementioned technical objects and other technical objects which are not mentioned will be apparently appreciated by those skilled in the art from the following description.

First, in summary of a feature of the present invention, an exemplary embodiment of the present invention provides a microwave processing method for focusing a microwave to collect and monitor thermal imaging information in a microwave apparatus, including: determining a microwave processing plan for focusing a microwave and thermally imaging with respect to a biological tissue subject using electromagnetic model information for permittivity and conductivity distribution for an anatomical image of the biological tissue subject; controlling a plurality of microwave transceivers to radiate a microwave signal having an amplitude and a phase value in accordance with the microwave processing plan through individual transceiving antennas to focus the microwave signal onto a specific part of the biological tissue subject; controlling some of the plurality of microwave transceivers and the remaining microwave transceivers to radiate the microwave signal and receive a scattering microwave at a predetermined period, in accordance with the microwave processing plan; and estimating a temperature change amount around the specific part of the biological tissue subject from the received scattering microwave to generate thermal imaging information for monitoring.

The microwave processing method may further include updating the microwave processing plan based on the feedback thermal imaging information.

The controlling to radiate the microwave signal and receive the scattering microwave may include stopping the radiation at a predetermined period in accordance with the microwave processing plan and controlling the remaining microwave transceivers to receive a scattering microwave scattered by the biological tissue subject through a transceiving antenna while one or more of the plurality of microwave transceivers radiate the microwave signal through the transceiving antennas.

The generating of thermal imaging information may include comparing an actual temperature change amount based on a sensing signal of one or more temperature sensors disposed around the biological tissue subject with the temperature change amount estimated from the scattering microwave, in order to verify or compensate for effectiveness of the temperature change amount estimated from the scattering microwave.

In order to update the microwave processing plan, an amplitude and a phase value of the microwave signal for focusing may be calculated through an electromagnetic analysis of the electromagnetic model information and the amplitude and the phase value may be calculated based on fast Fourier transform (FFT) on the scattering microwave.

In order to update the microwave processing plan, an amplitude and a phase value of the microwave signal for focusing may be calculated through an electromagnetic analysis of the electromagnetic model information and the amplitude and the phase value may be calculated by analyzing electric field distribution of the transceiving antennas which radiate the microwave signal.

In order to obtain thermal imaging information including the temperature change amount around the specific part of the biological tissue subject, an amplitude or a phase of the scattering microwave may be measured between two times having a predetermined interval and a distribution image of a temperature change amount including a temperature change amount distribution around the specific part in the biological tissue subject may be obtained from a difference between the amplitudes or the phases between the two times.

Another exemplary embodiment of the present invention provides a microwave apparatus for focusing a microwave to collect and monitor thermal imaging information, including: a plurality of transceiving antennas which is arranged around a biological tissue subject; a plurality of microwave transceivers which transmits and receives a microwave signal through the plurality of transceiving antennas; a signal processing and control unit which determines a microwave processing plan for focusing a microwave and thermally imaging with respect to a biological tissue subject using electromagnetic model information for permittivity and conductivity distribution for an anatomical image of the biological tissue subject; a microwave supplier which supplies the microwave signal in accordance with control of the signal processing and control unit; a microwave distributor which distributes outputs of the microwave supplier to the plurality of microwave transceivers; and a microwave receiver which receives and processes the microwave signal received by the plurality of microwave transceivers through the plurality of transceiving antennas to output the microwave signal to the signal processing and control unit, in which the signal processing and control unit may control the plurality of microwave transceivers to radiate a microwave signal having an amplitude and a phase value in accordance with the microwave processing plan through individual transceiving antennas to focus the microwave signal onto a specific part of the biological tissue subject; and control some of the plurality of microwave transceivers and the remaining microwave transceivers to radiate the microwave signal and receive the scattering microwave at a predetermined period in accordance with the microwave processing plan to estimate a temperature change amount around the specific part of the biological tissue subject from the received scattering microwave to generate thermal imaging information for monitoring.

The signal processing and control unit may update the microwave processing plan based on the feedback thermal imaging information.

The signal processing and control unit in order to radiate the microwave signal and receive the scattering microwave, may stop the radiation at a predetermined period, in accordance with the microwave processing plan, and control the remaining microwave transceivers to receive the scattering microwave scattered from the biological tissue subject through the transceiving antennas, while one or more of the plurality of microwave transceivers radiate the microwave signal through the transceiving antennas.

The microwave apparatus may further include one or more temperature sensors which are disposed around the biological tissue subject; and a temperature signal receiver which receives and processes a sensing signal from the one or more temperature sensors to output the sensing signal to the signal processing and control unit, the signal processing and control unit may compare an actual temperature change amount based on the sensing signal of the one or more temperature sensors with the temperature change amount estimated from the scattering microwave in order to verify or compensate for effectiveness of the temperature change amount estimated from the scattering microwave.

In order to update the microwave processing plan, the signal processing and control unit may calculate an amplitude and a phase value of the microwave signal for focusing through an electromagnetic analysis of the electromagnetic model information and calculate the amplitude and the phase value based on fast Fourier transform (FFT) on the scattering microwave.

In order to update the microwave processing plan, the signal processing and control unit may calculate an amplitude and a phase value of the microwave signal for focusing through an electromagnetic analysis of the electromagnetic model information and calculate the amplitude and the phase value by analyzing electric field distribution of the transceiving antennas which radiate the microwave signal.

In order to obtain thermal imaging information including the temperature change amount around the specific part of the biological tissue subject, the signal processing and control unit may measure an amplitude or a phase of the scattering microwave between two times having a predetermined interval and obtain a distribution image of a temperature change amount including a temperature change amount distribution around the specific part in the biological tissue subject from a difference between the amplitudes or the phases between the two times.

Each of the plurality of microwave transceivers may include a signal amplifier which amplifies the microwave signal provided through the microwave distributor in accordance with control of the signal processing and control unit; a phase shifter which shifts a phase of the microwave signal output from the signal amplifier in accordance with the control of the signal processing and control unit; and a transceiving switch which selectively receives the microwave signal from the transceiving antennas or transmits the microwave signal output from the phase shifter to the transceiving antennas.

According to the microwave signal processing method and apparatus of the present invention, the microwave is focused on a specific part in and out of a biological tissue and an internal temperature change of the biological tissue caused thereby is rapidly imaged and monitored, so that focusing accuracy is improved.

Figure 1:
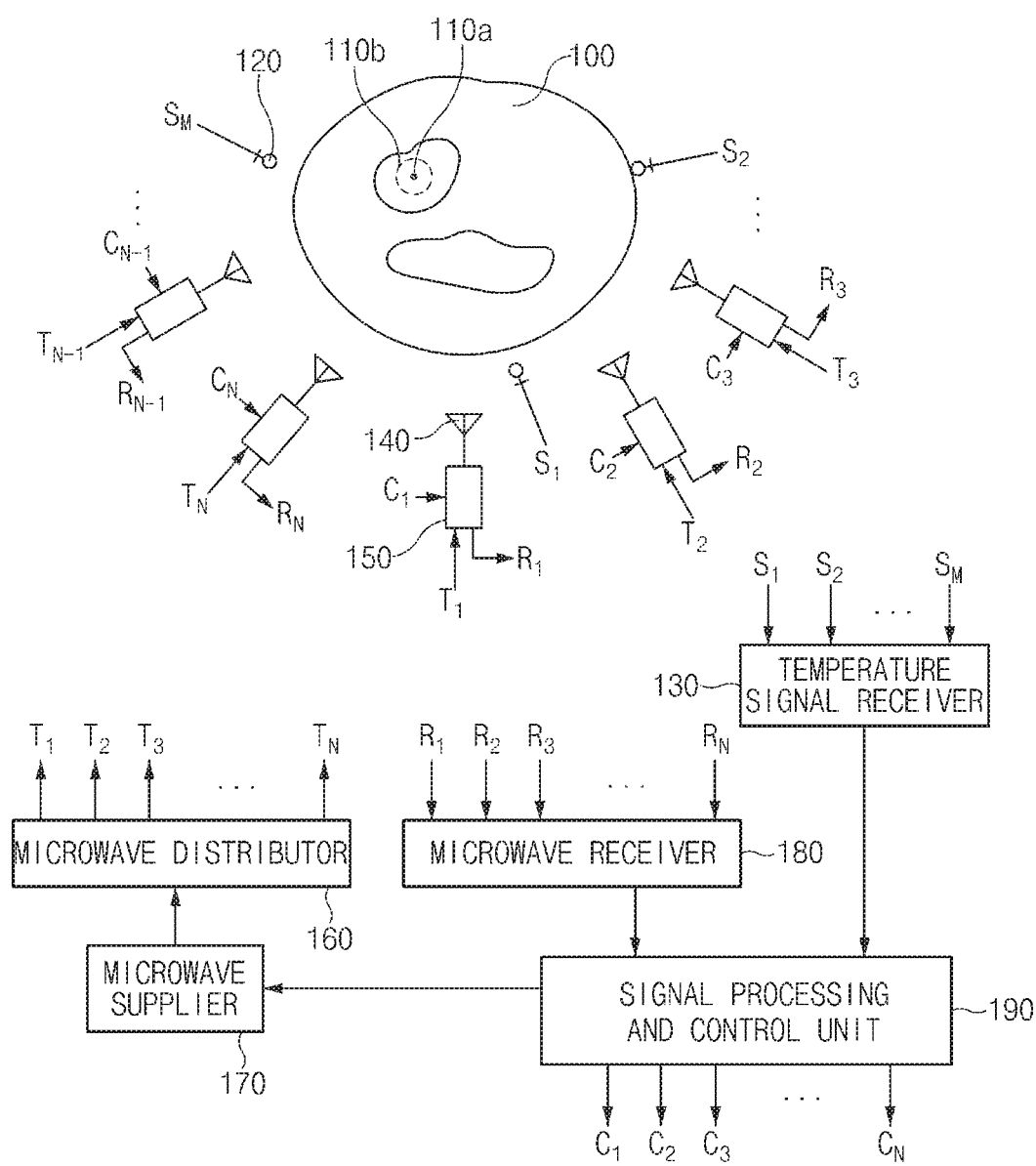
FIG. 1 is a configuration diagram of a microwave apparatus for focusing a microwave and imaging heat according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, some embodiments of the present invention will be described in detail with reference to the accompanying drawings. In the figures, even though the like parts are illustrated in different drawings, it should be understood that like reference numerals refer to the same parts. In describing the embodiments of the present invention, when it is determined that the detailed description of the known configuration or function related to the present invention may obscure the understanding of embodiments of the present invention, the detailed description thereof will be omitted.

In describing components of the exemplary embodiment of the present invention, terminologies such as first, second, A, B, (a), (b), and the like may be used. However, such terminologies are used only to distinguish a component from another component but nature or an order of the component is not limited by the terminologies. If it is not contrarily defined, all terminologies used herein including technological or scientific terms have the same meaning as those generally understood by a person with ordinary skill in the art. Terminologies which are defined in a generally used dictionary should be interpreted to have the same meaning as the meaning in the context of the related art but are not interpreted as ideal or excessively formal meaning if they are not clearly defined in the present invention.

FIG. 1 is a configuration diagram of a microwave apparatus 500 for focusing a microwave and imaging heat according to an exemplary embodiment of the present invention.

Referring to FIG. 1, in order to apply spherical continuous microwave 110b which is focused on a specific part 110a of a biological tissue subject 100 and obtain thermal imaging, a microwave apparatus 500 according to an exemplary embodiment of the present invention includes one or more temperature sensors 120 which measure a temperature of a skin or a peripheral part of the biological tissue subject 100, a plurality of transceiving antennas 140 disposed around the biological tissue subject 100, and a plurality of microwave transceivers 150 which transmits/receives microwaves through the plurality of transceiving antennas 140. In addition, the microwave apparatus 500 includes a temperature signal receiver 130, a microwave distributor 160, a microwave supplier 170, a microwave receiver 180, and a signal processing and control unit 190.

The signal processing and control unit 190 controls the microwave supplier 170 to supply a microwave signal to the microwave distributor 160 and the microwave distributor 160 distributes the microwave signal supplied from the microwave supplier 170 to provide the distributed signals $T_1$ to $T_N$ to the microwave transceivers 150.

The microwave receiver 180 receives and processes microwave signals $R_1$ to $R_N$ which are received by the microwave transceivers 150 through the antennas 140 to output the signals to the signal processing and control unit 190. The temperature signal receiver 130 receives and processes a sensed signal(s) $S_1$ to $S_M$ from the temperature sensor(s) 120 to output the signals to the signal processing and control unit 190. N and M are natural numbers.

The signal processing and control unit 190 collects signals received from the microwave receiver 180 and the temperature signal receiver 130 and generates control signals $C_1$ to $C_N$ in accordance with a predetermined algorithm based on the collected signals to control the microwave transceiver 150 and controls the microwave supplier 170 to generate the microwave signal.

Figure 2:
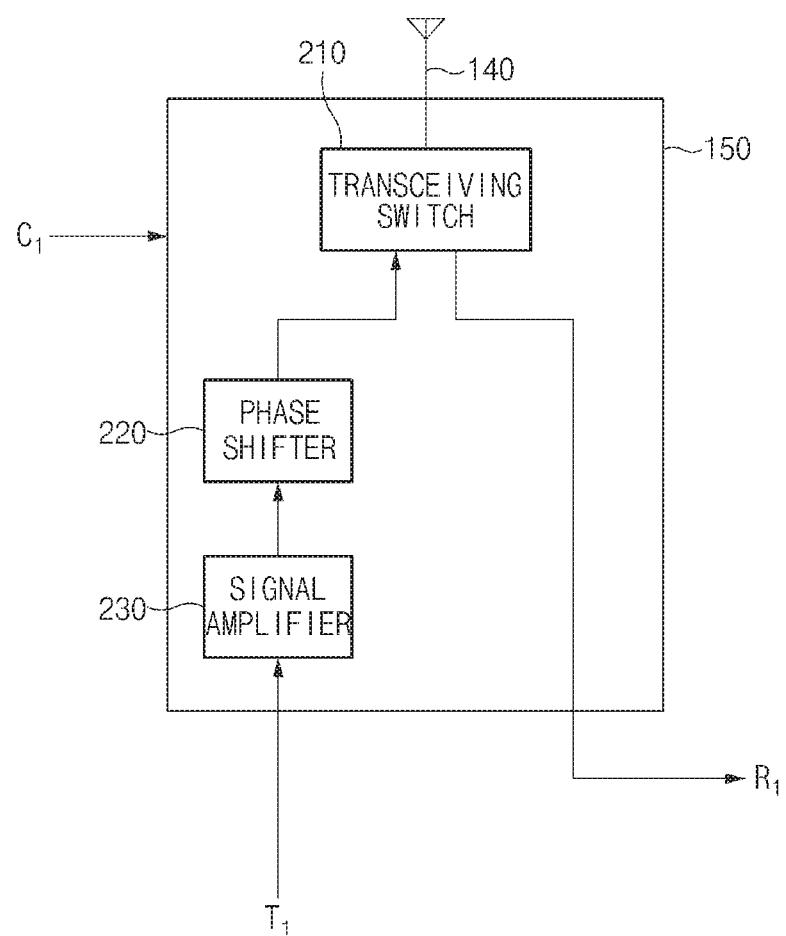
FIG. 2 is a detailed configuration diagram of a microwave transceiver of FIG. 1.

FIG. 2 is a detailed configuration diagram of a microwave transceiver 150 of FIG. 1.

Referring to FIG. 2, the microwave transceiver 150 according to an exemplary embodiment of the present invention includes a transceiving switch 210, a phase shifter 220, and a signal amplifier 230.

The transceiving switch 210 which is connected to the transceiving antennas 140 selectively receives the microwave signal from the transceiving antennas 140 or transmits the microwave signal output from the phase shifter 220 to the transceiving antennas 140, in accordance with the control signal (for example, $C_1$) from the signal processing and control unit 190.

The signal amplifier 230 amplifies the microwave signal (for example $T_1$) provided through the microwave distributor 160 to have a predetermined amplitude in accordance with the control signal (for example $C_1$) from the signal processing and control unit 190 and the phase shifter 220 converts and outputs a phase of the microwave signal output from the signal amplifier 230 to have a predetermined value to output the microwave signal, in accordance with the control signal (for example, $C_1$) from the signal processing and control unit 190.

Hereinafter, referring to the flowchart of FIG. 3, a microwave focusing and thermal imaging operation of the microwave apparatus 500 according to an exemplary embodiment of the present invention will be described in more detail.

Figure 3:
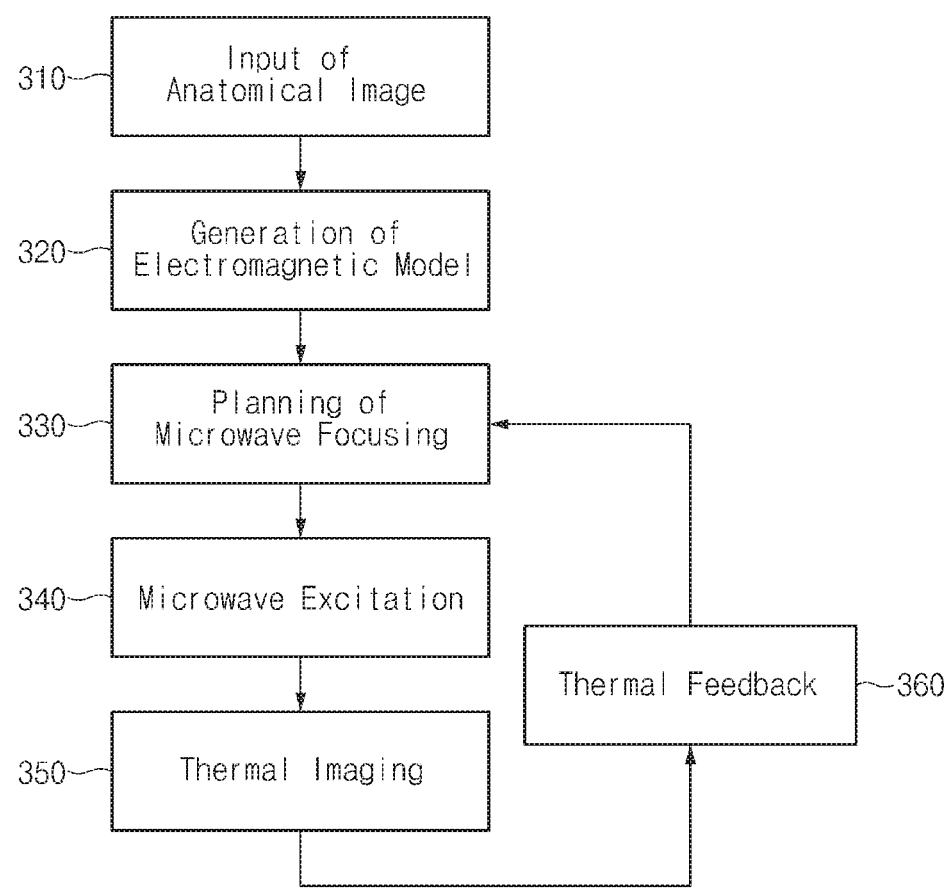
FIG. 3 is a flowchart of a microwave focusing and thermal imaging operation of a microwave apparatus according to an exemplary embodiment of the present invention.

FIG. 3 is a flowchart of a microwave focusing and thermal imaging operation of the microwave apparatus 500 according to an exemplary embodiment of the present invention.

Figure 4:
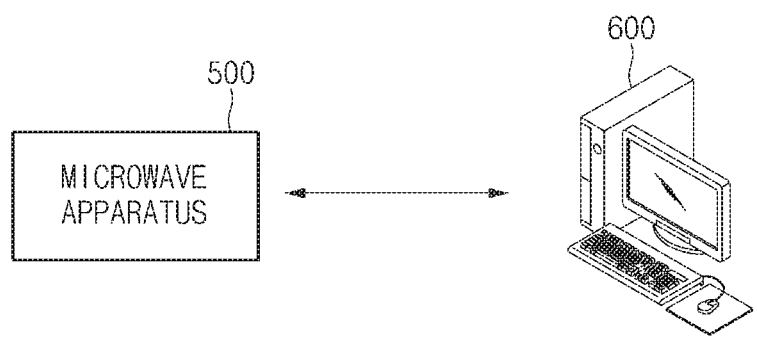
FIG. 4 is a view illustrating a relationship between a microwave apparatus according to an exemplary embodiment of the present invention and an external control system.

First, an external control system (see, 600 of FIG. 4) such as a computer is connected to the microwave apparatus 500 of the present invention and the external control system 600 is driven to transmit predetermined data required to drive the microwave apparatus 500 of the present invention to the microwave apparatus 500 and set predetermined setting values.

Referring to FIG. 3, for the purpose of microwave focusing and thermal imaging, first, an anatomical image of a biological tissue subject 100 is obtained in step 310. The anatomical image of the biological tissue subject 100 may be obtained using a device for obtaining a magnetic resonance image (MRI), a computed tomography (CT) image, or a microwave tomography (MT) image by a microwave. In some cases, when the biological tissue subject is a biological tissue subject which may be standardized, such as a head, an image for a general standard model may be used. An anatomical image prepared for the liver, stomach, appendix, large intestine, esophagus, small intestine, or head for biopsy or treatment as described above may be displayed on a display device of the external control system 600.

When the anatomical image is obtained, the external control system 600 such as a computer generates electromagnetic model information having information of permittivity and conductivity for the anatomical image in step 320. The electromagnetic model information may be distribution information of permittivity and conductivity of the biological tissue subject 100 which is estimated in accordance with a predetermined biological tissue analysis method. In some cases, the signal processing and control unit 190 may generate the electromagnetic model information for the anatomical image.

The signal processing and control unit 190 determines a microwave amplitude and phase value and a microwave processing plan such as a microwave transceiving plan (a radiation time and a thermal imaging period) in accordance with a predetermined algorithm for focusing the microwave onto the biological tissue subject 100 and thermally imaging using the electromagnetic model information, to control to focus the microwave onto the specific part 110a of the biological tissue subject 100 and to acquire thermally imaging information in step 330.

The signal processing and control unit 190 controls the microwave supplier 170 to supply the microwave signal to the microwave distributor 160 in accordance with the microwave processing plan and the microwave distributor 160 distributes the microwave signal supplied from the microwave supplier 170 to provide the distributed signals $T_1$ to $T_N$ to the microwave transceivers 150. The microwave transceivers 150 radiate the microwave signal having the amplitude and the phase value through the transceiving antennas 140 for a predetermined time in accordance with the control signals $C_1$ to $C_N$ based on the microwave processing plan to focus the microwave on the specific part 110a of the biological tissue subject 100 in step 340.

In this case, in order to image an internal temperature of the biological tissue subject 100, the signal processing and control unit 190 intermittently stops the microwave radiation of step 340 in accordance with a predetermined period (thermal imaging period) in accordance with the microwave processing plan, and controls one or more remaining microwave transceivers 150 to receive scattering microwaves scattered from the biological tissue subject 100 through the transceiving antennas while one or more of the microwave transceivers 150 radiate the microwave signal having the amplitude and the phase value through the transceiving antennas in accordance with the control signals of the signal processing and control unit 190.

The microwave receiver 180 receives and processes the scattering microwave signal(s) which is (are) received by the microwave transceiver(s) 150 to output the signals to the signal processing and control unit 190 and the temperature signal receiver 130 receives and processes the sensing signal(s) $S_1$ to $S_M$ from the temperature sensor(s) 120 to output the signals to the signal processing and control unit 190. Therefore, while some of the microwave transceivers radiate and focus the microwave signal, the signal processing and control unit 190 analyzes the scattering microwave signal(s) and the sensing signal(s) in accordance with a predetermined imaging algorithm to estimate an internal temperature of the biological tissue subject 100, that is, an ambient temperature change amount with respect to the specific part 110a to generate thermal imaging information in step 350. In such a microwave thermal imaging step, in order to verify effectiveness of a temperature change amount of the thermal imaging information for every time, the signal processing and control unit 190 may further perform a step of comparing the temperature with an actual temperature change amount based on the sensing signal(s) of the temperature sensor 120 disposed around the biological tissue subject 100. For example, when a comparison result indicates that the temperatures are similar in a predetermined range, the signal processing and control unit 190 outputs the thermal imaging information. Otherwise, the signal processing and control unit 190 generates an error message and compensates for the thermal imaging information (temperature change amount) based on the sensing signal(s) of the temperature sensor 120 in some cases. The thermal imaging information is transmitted to the external control system 600 to be displayed on the display device together with the anatomical image so that heat generated around the specific part 110a of the biological tissue subject 100 may be monitored.

As described above, when the temperature change amount in the biological tissue subject 100 which is monitored in accordance with the microwave thermal imaging result is feedbacked, the signal processing and control unit 190 updates the microwave processing plan which adjusts the amplitude and the phase value of the microwave and the microwave processing plan in accordance with the predetermined algorithm to control to repeat the above process in step 360.

Similarly to step 330, an example of a method for determining the microwave processing plan such as amplitude and a phase value of a microwave which is radiated through the microwave transceiver 150 in order to focus the microwave onto the specific part 110a of the biological tissue subject 100 will be described.

First, the signal processing and control unit 190 calculates a phase and an amplitude to apply a virtual spherical continuous microwave 110b so as to make the specific part 110a be at a focusing position through the electromagnetic analysis of the electromagnetic model information of the biological tissue subject 100. In this case, in step 360, the signal processing and control unit 190 reflects the temperature change amount in the biological tissue subject 100 in accordance with the feedback thermal imaging information to adjust a time for the microwave transceiver 140 to radiate the microwave signal.

For example, in order to electromagnetically analyze the electromagnetic model information, when the microwave signal is radiated through some of the transceiving antennas 140 in step 350, the signal processing and control unit 190 collects arbitrary scattering microwave signal through the microwave receiver 180 and performs fast Fourier transform (FFT) on the collected scattering microwave signal to calculate the phase and the amplitude. After changing a sign of the phase calculated as described above (for example, reflecting a reflective wave) and normalizing the calculated amplitude to be a predetermined value, an inverse number (1/(normalized amplitude value)) thereof is obtained. The amplitude and phase value calculated as described above are used to control the signal amplifier 230 and the phase shifter 220 of the microwave transceiver 140 in order to make the specific part 110a be a focusing position. In this case, when the microwave amplitude value determined as described above exceeds an available range, an external tissue of the biological tissue subject 100 may suffer a burn. Therefore, in order to prevent the burn, the amplitude value for controlling the signal amplifier 230 may be limited so as not to exceed a predetermined threshold value.

Similarly to step 330, another example of a method for determining the microwave processing plan such as amplitude and a phase value of a microwave which is radiated through the microwave transceiver 150 in order to focus the microwave onto the specific part 110a of the biological tissue subject 100 will be described.

When the microwave signal is radiated through some of the transceiving antennas 140 in step 350, the signal processing and control unit 190 may calculate distribution of an electric field generated in each antenna 140 which radiates the microwave signal from the electromagnetic analysis. The signal processing and control unit 190 may determine the amplitude and the phase value of the microwave which allows the distribution of the electric field to be concentrated onto the specific part of the subject 100 and not to exceed the predetermined limit in other parts with respect to the electromagnetic model information of the biological tissue subject 100 through a predetermined optimization algorithm, using the calculated electric field distribution.

Similarly to the microwave thermal imaging step 350, an example of a method for imaging an internal temperature change amount of the biological tissue subject 100 will be described.

For example, when the microwave signal is radiated through some of the transceiving antennas 140 in step 350, the signal processing and control unit 190 transmits a predetermined microwave signal between antennas 140 and receives the scattering microwave at a reference time t0 before the temperature of the biological tissue subject 100 is changed to measure amplitude/phase values of the received signal and stores the amplitude/phase values in a storing unit of the external control system 600 such as a computer. Next, in a microwave thermal imaging step 350 which is intermittently performed in accordance with a predetermined period, the signal processing and control unit 190 similarly transmits a predetermined microwave signal between the antennas 140 and receives the scattering microwave at an arbitrary time t1 to measure amplitude/phase values of the received signal. Therefore, with respect to measured data difference y of the amplitude or the phase values between t0 and t1 having a predetermined interval, a distribution image x of a temperature change amount in the biological tissue subject 100 may be estimated through a predetermined optimization algorithm. The distribution image x of the temperature change amount as thermal imaging information may indicate distribution of an ambient temperature change amount with respect to the specific part 110*a*.

For example, a relationship between a vector y for a data difference measured by the antennas 140 at arbitrary two times t0 and t1 and a vector x for a distribution image of the temperature change amount measured by the antennas 140 at arbitrary two times t0 and t1 may be represented by a linear relationship of Equation 1. A may be a vector of a characteristic parameter related with the individual antennas 140.

$$y = Ax \quad \text{[Equation 1]}$$

In this case, in order to minimize the difference between the vectors Ax and y, a function F(x) is defined in advance as represented in Equation 2. The signal processing and control unit 190 may calculate an optimal vector x which minimizes F(x). $\lambda_1$ and $\lambda_2$ are user input parameters for tuning a quality of the temperature distribution image x.

$$F(x) = \|Ax - y\|_2^2 + \lambda_2 \|x\|_2^2 + \lambda_1 \|x\|_1$$

$$\|x\|_p = (\Sigma_i |x_i|^p)^{1/p} \quad \text{[Equation 2]}$$

In such a microwave thermal imaging step, in order to verify thermal imaging information with respect to the temperature change amount for every time, the signal processing and control unit 190 may further perform a step of comparing the temperature with an actual temperature change amount based on the sensing signal(s) of the temperature sensor 120 disposed around the biological tissue subject 100. For example, when a comparison result indicates that the temperatures are similar in a predetermined range, the signal processing and control unit 190 outputs the thermal imaging information. Otherwise, the signal processing and control unit 190 generates an error message and compensates for the thermal imaging information (temperature change amount) based on the sensing signal(s) of the temperature sensor 120 in some cases.

As described above, in the microwave apparatus 100 of the present invention, the microwave is focused on a specific part in and out of a biological tissue and images and monitors at a high speed an internal temperature change of the biological tissue caused thereby, so that focusing accuracy is improved.

It will be appreciated that various exemplary embodiments of the present invention have been described herein for purposes of illustration, and that various modifications, changes, and substitutions may be made by those skilled in the art without departing from the scope and spirit of the present disclosure.

Accordingly, the exemplary embodiments disclosed herein are intended to not limit but describe the technical spirit of the present invention and the scope of the technical spirit of the present invention is not restricted by the exemplary embodiments. The protection scope of the present invention should be interpreted based on the following appended claims and it should be appreciated that all technical spirits included within a range equivalent thereto are included in the protection scope of the present invention.

What is claimed is:

1. A microwave processing method for focusing a microwave to collect and monitor thermal imaging information in a microwave apparatus, the method comprising:
   determining a microwave processing plan for focusing a microwave and thermally imaging with respect to a biological tissue subject using electromagnetic model information for permittivity and conductivity distribution for an anatomical image of the biological tissue subject;
   controlling a plurality of microwave transceivers to radiate a microwave signal having an amplitude and a phase value in accordance with the microwave processing plan through individual transceiving antennas to focus the microwave signal onto a specific part of the biological tissue subject;
   controlling some of the plurality of microwave transceivers and the remaining microwave transceivers to radiate the microwave signal and receive a scattering microwave at a predetermined period, in accordance with the microwave processing plan; and
   estimating a temperature change amount around the specific part of the biological tissue subject from the received scattering microwave to generate thermal imaging information for monitoring,
   wherein the microwave processing plan comprises processing the amplitude and the phase value of the microwave which is radiated through the individual transceiving antennas in order to focus the microwave onto the specific part of the biological tissue subject.

2. The method of claim 1, further comprising: updating the microwave processing plan based on the feedback thermal imaging information.

3. The method of claim 1, wherein the controlling to radiate the microwave signal and receive the scattering microwave includes, stopping the radiation at a predetermined period in accordance with the microwave processing plan and controlling the remaining microwave transceivers to receive a scattering microwave scattered by the biological tissue subject through a transceiving antenna while one or more of the plurality of microwave transceivers radiate the microwave signal through the transceiving antennas.

4. The method of claim 1, wherein the generating of thermal imaging information includes comparing an actual temperature change amount based on a sensing signal of one or more temperature sensors disposed around the biological tissue subject with the temperature change amount estimated from the scattering microwave, in order to verify or compensate for effectiveness of the temperature change amount estimated from the scattering microwave.

5. The method of claim 2, wherein in order to update the microwave processing plan, an amplitude and a phase value of the microwave signal for focusing are calculated through an electromagnetic analysis of the electromagnetic model information and the amplitude and the phase value are calculated based on fast Fourier transform (FFT) on the scattering microwave.

6. The method of claim 2, wherein in order to update the microwave processing plan, an amplitude and a phase value of the microwave signal for focusing are calculated through an electromagnetic analysis of the electromagnetic model information and the amplitude and the phase value are calculated by analyzing electric field distribution of the transceiving antennas which radiate the microwave signal.

7. The method of claim 1, wherein in order to obtain thermal imaging information including the temperature change amount around the specific part of the biological tissue subject, an amplitude or a phase of the scattering microwave is measured between two times having a predetermined interval and a distribution image of a temperature change amount including a temperature change amount distribution around the specific part in the biological tissue subject is obtained from a difference between the amplitudes or the phases between the two times.

8. A microwave apparatus for focusing a microwave to collect and monitor thermal imaging information, the apparatus comprising:
  a plurality of transceiving antennas which is arranged around a biological tissue subject;
  a plurality of microwave transceivers which transmits and receives a microwave signal through the plurality of transceiving antennas;
  a signal processing and control unit which determines a microwave processing plan for focusing a microwave and thermally imaging with respect to a biological tissue subject using electromagnetic model information for permittivity and conductivity distribution for an anatomical image of the biological tissue subject;
  a microwave supplier which supplies the microwave signal in accordance with control of the signal processing and control unit;
  a microwave distributor which distributes outputs of the microwave supplier to the plurality of microwave transceivers; and
  a microwave receiver which receives and processes the microwave signal received by the plurality of microwave transceivers through the plurality of transceiving antennas to output the microwave signal to the signal processing and control unit,
  wherein the signal processing and control unit:
    controls the plurality of microwave transceivers to radiate a microwave signal having an amplitude and a phase value in accordance with the microwave processing plan through individual transceiving antennas to focus the microwave signal onto a specific part of the biological tissue subject; and
    controls some of the plurality of microwave transceivers and the remaining microwave transceivers to radiate the microwave signal and receive the scattering microwave at a predetermined period in accordance with the microwave processing plan to estimate a temperature change amount around the specific part of the biological tissue subject from the received scattering microwave to generate thermal imaging information for monitoring,
  wherein the microwave processing plan comprises processing the amplitude and the phase value of a microwave which is radiated through the individual transceiving antennas in order to focus the microwave onto the specific part of the biological tissue subject.

9. The apparatus of claim 8, wherein the signal processing and control unit updates the microwave processing plan based on the feedback thermal imaging information.

10. The apparatus of claim 8, wherein in order to radiate the microwave signal and receive the scattering microwave, the signal processing and control unit stops the radiation at a predetermined period, in accordance with the microwave processing plan, and controls the remaining microwave transceivers to receive the scattering microwave scattered from the biological tissue subject through the transceiving antennas, while one or more of the plurality of microwave transceivers radiate the microwave signal through the transceiving antennas.

11. The apparatus of claim 8, further comprising:
  one or more temperature sensors which are disposed around the biological tissue subject; and
  a temperature signal receiver which receives and processes a sensing signal from the one or more temperature sensors to output the sensing signal to the signal processing and control unit,
  wherein the signal processing and control unit compares an actual temperature change amount based on the sensing signal of the one or more temperature sensors with the temperature change amount estimated from the scattering microwave in order to verify or compensate for effectiveness of the temperature change amount estimated from the scattering microwave.

12. The apparatus of claim 9, wherein in order to update the microwave processing plan, the signal processing and control unit calculates an amplitude and a phase value of the microwave signal for focusing through an electromagnetic analysis of the electromagnetic model information and calculates the amplitude and the phase value based on fast Fourier transform (FFT) on the scattering microwave.

13. The apparatus of claim 9, wherein in order to update the microwave processing plan, the signal processing and control unit calculates an amplitude and a phase value of the microwave signal for focusing through an electromagnetic analysis of the electromagnetic model information and calculates the amplitude and the phase value by analyzing electric field distribution of the transceiving antennas which radiate the microwave signal.

14. The apparatus of claim 8, wherein in order to obtain thermal imaging information including the temperature change amount around the specific part of the biological tissue subject, the signal processing and control unit measures an amplitude or a phase of the scattering microwave between two times having a predetermined interval and obtains a distribution image of a temperature change amount including a temperature change amount distribution around the specific part in the biological tissue subject from a difference between the amplitudes or the phases between the two times.

15. The apparatus of claim 8, wherein each of the plurality of microwave transceivers includes:
  a signal amplifier which amplifies the microwave signal provided through the microwave distributor in accordance with control of the signal processing and control unit;
  a phase shifter which shifts a phase of the microwave signal output from the signal amplifier in accordance with the control of the signal processing and control unit; and
  a transceiving switch which selectively receives the microwave signal from the transceiving antennas or transmits the microwave signal output from the phase shifter to the transceiving antennas.

* * * * *